United States Patent [19]

Okuhara et al.

[11] Patent Number: 4,977,138
[45] Date of Patent: Dec. 11, 1990

[54] FR901228 SUBSTANCE AND PREPARATION THEREOF

[75] Inventors: Masakuni Okuhara; Toshio Goto; Yasuhiro Hori, all of Tsukuba; Takashi Fujita, Tsuchiura; Hirotsugu Ueda; Nobuharu Shigematsu, both of Tsukuba, all of Japan

[73] Assignee: Fujisawa Pharmaceutical Co., Ltd., Osaka, Japan

[21] Appl. No.: 375,998

[22] Filed: Jul. 6, 1989

[30] Foreign Application Priority Data

Jul. 26, 1988 [GB] United Kingdom ................ 8817743

[51] Int. Cl.$^5$ ...................... A61K 37/02; C07K 7/54
[52] U.S. Cl. ..................... 514/10; 530/317; 530/323
[58] Field of Search .................... 530/317, 323; 514/9, 514/10

[56] References Cited

U.S. PATENT DOCUMENTS 4,785,078 11/1988 Fiese et al. .......................... 530/317
4,816,559 3/1989 Harada et al. ...................... 530/317

Primary Examiner—John W. Rollins
Assistant Examiner—Christina Chan
Attorney, Agent, or Firm—Oblon, Spivak, McClelland, Maier & Neustadt

[57] ABSTRACT

The invention relates to a compound having antimicrobial and antitumor activity, the compound being designated FR901228 substance of the following formula:

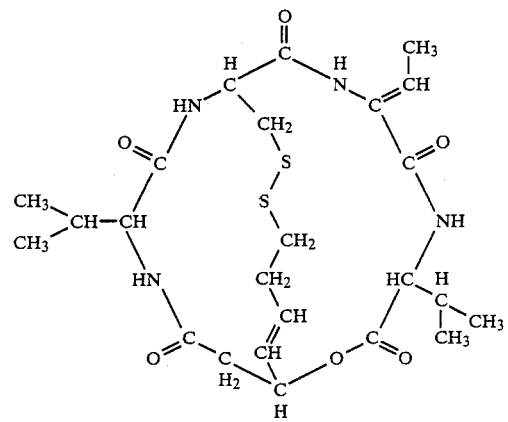

2 Claims, 3 Drawing Sheets

FR901228 SUBSTANCE AND PREPARATION THEREOF

This invention relates to a new compound having a biological activity, hereinafter referred to as FR901228 substance. More particularly, this invention relates to a new biologically active FR901228 substance, which has antimicrobial and antitumor activities, to a process for its preparation, and to pharmaceutical compositions comprising the same.

FR901228 substance of this invention can be produced by fermentation of FR901228 substance-producing strain belonging to the genus Chromobacterium such as *Chromobacterium violaceum* WB968 in a nutrient medium.

The fermentation process is explained in detail in the following.

(1) Microorganism:

Particulars of the microorganism used for producing FR901228 substance is explained in the following.

Taxonomic studies on the strain WB968:

Strain WB968 was isolated from a soil sample obtained from Yamagata-ken, JAPAN.

The methods described in Bergey's Manual of Systematic Bacteriology (Volume 1) were employed principally for this taxonomic study.

(i) Morphological characteristics

Morphological observation of the strain WB968 was carried out by the optical and electron microscopes with cells cultured on nutrient broth and agar at 30° C. for 20

Strain WB968 was a gram-negative, motile bacterium. The cell shapes were rod and about $0.5-0.6 \times 1.2-1.8$ $\mu$m in Results were shown in Table 1.

TABLE 1
Morphological characteristics of stain WB968

| | |
|---|---|
| Gram stain | negative |
| color of colony | grayish orange |
| cell shape | rod |
| cell size | $0.5-0.6 \times 1.2-1.8$ $\mu$m |
| spore | negative |
| motility | positive |
| flagella | single polar flagellum |

(ii) Physiological characteristics

Physiological characteristics of the strain WB968 were summarized in Table 2. The growth temperature range was from 15° C. to 40° C.

The strain WB968 was oxidase positive, catalase positive and O-F test fermentative. Casein was hydrolyzed and esculin hydrolysis was negative. Glucose, fructose and trehalose were fermented. Indole test was negative. Voges-Preskauer test was negative. And α-galactosidase test (ONPG test) was negative.

TABLE 2
Physiological characteristics of the strain WB968

| Conditions | Characteristics |
|---|---|
| growth temperature | 15–40° C. |
| growth in air | positive |
| growth in peptone water without NaCl | positive |
| growth in 6% NaCl | negative |
| growth in KCN broth | positive |
| violet pigment | negative |
| catalase | positive |
| oxidase | positive |
| O—F test | fermentative |
| gas from glucose | negative |
| 0/129 sensitivity (10, 150 μg) | negative |
| nitrate reaction | positive |
| Tween 80 esterase | positive |
| H$_2$S production (TSI) | negative |
| indole | negative |
| MR | negative |
| VP | negative |
| Simons citrate | positive |
| ONPG test | negative |
| urease | positive |
| DNase | positive |
| starch hydrolysis | negative |
| gelatin liquefaction | positive |
| casein hydrolysis | positive |
| esculin hydrolysis | negative |
| lysin decarboxylase | negative |
| ornithine decarboxylase | negative |
| arginine dihydrolase | positive |
| G + C content of DNA | 62.7 mol % |
| major cellular fatty acid | C$_{16:1}$ |
| quinone type | Q-8 |
| acid from sugar | |
| D-glucose | positive |
| L-arabinose | negative |
| D-mannitol | negative |
| D-fructose | positive |
| D-galactose | negative |
| D-sorbitol | negative |
| D-trehalose | positive |
| sucrose | negative |
| lactose | negative |
| salicin | negative |
| maltose | negative |
| cellobiose | negative |

(iii) Identification

According to Bergey's Manual of Systematic Bacteriology (Volume 1), the strain WB968 was identified as *Chromobacterium violaceum* from those characteristics described above.

A culture of *Chromobacterium violaceum* WB968 has been deposited with Fermentation Research Institute Agency of Industrial Science and Technology (1-3, Higashi 1 chome Tsukuba-shi, IBARAKI, 305 JAPAN) on July 20, 1988 under the number of FERM BP-1968 under Budapest Treaty route.

(2) Production of FR901228 substance

FR901228 substance of this invention is produced when a FR901228 substance-producing strain belonging to the genus Chromobacterium (e. g. *Chromobacterium violaceum* WB968) is grown in a nutrient medium containing sources of assimilable carbon and nitrogen under aerobic conditions (e. g. shaking culture, submerged culture, etc.).

The preferred sources of carbon in the nutrient medium are carbohydrates such as glucose, starch, fructose or glycerin.

The preferred sources of nitrogen are bouillon, yeast extract, peptone, gluten meal, cotton seed flour, soybean meal, corn steep liquor, dried yeast, wheat germ, etc., as well as inorganic and organic nitrogen compounds such as ammonium salts (e. g. ammonium nitrate, ammonium sulfate, ammonium phosphate, etc.), urea or amino acid.

The carbon and nitrogen sources, though advantageously employed in combination, need not to be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, or cobalt salts.

If necessary, especially when the culture medium foams seriously a defoaming agent, such as liquid paraffin, fatty oil, plant oil, mineral oil or silicone may be added.

As in the case of the preferred methods used for the production of other biologically active substances in massive amounts, submerged aerobic cultural conditions are preferred for the production of FR901228 substance in massive amounts.

For the production in small amounts, a shaking culture in a flask is employed.

Further, when the growth is carried out in large tanks, it is preferable to use the vegetative cells of the bacterium for inoculation in the production tanks in order to avoid growth lag in the process of production of FR901228 substance. Accordingly, it is desirable first to produce a vegetative cells of the bacterium by inoculating a relatively small quantity of culture medium with cells of the bacterium and culturing said inoculated medium, and then to transfer the cultured vegetative cells to large tanks. The medium, in which the vegetative cells is produced, is substantially the same as or different from the medium utilized for the production of FR901228 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture The fermentation is usually conducted at a temperature between about 10° C. and 40° C., preferably 25° C. to 35° C., for a period of about 15 hours to 50 hours, which may be varied according to fermentation conditions and scales.

When the fermentation is completed, the culture broth is then subjected for the recovery of FR901228 substance to various processes conventionally used for recovery and purification of biological active substances, for instance, solvent extraction with an appropriate solvent or a mixture of some solvents, chromatography or recrystallization from an appropriate solvent or a mixture of some solvents According to this invention, in general, FR901228 substance is found mainly in the cells of the bacterium. But the filtrate also includes FR901228 substance. Accordingly, it is preferable that the whole culture broth is directly subjected to the isolation process of FR901228 substance, for example, by means of extraction using an appropriate solvent such as hot water, acetone or ethyl acetate, or a mixture of these solvents The extract is treated by a conventional manner to provide FR901228 substance, for example, the extract is concentrated by evaporation or distillation to a smaller amount and the resulting residue containing active material, i. e. FR901228 substance is purified by conventional purification processes, for example, chromatography or recrystallization from an appropriate solvent or a mixture of some solvents.

Physico-chemical properties of FR901228 substance are shown in FIGS. 1—3.

FR901228 substance as obtained according to the aforementioned fermentation process has the following physico-chemical properties.

Appearance: colorless prisms.

Nature: neutral substance.

Melting point: 235°–245° c. (dec).

Specific rotation: $[\alpha]_D^{23}$ :+39° (C=1.0, CHCl$_3$). (c=1.0, CHCl$_3$).

Molecular formula: $C_{24}H_{36}N_4O_6S_2$.

Elemental Analysis: Calcd: for $C_{24}H_{36}N_4O_6S_2 \cdot CH_3CN$: C, 53.68; H, 6.76; N, 12.04; S, 11.02 (%). Found: C, 53.68; H, 6.71; N, 11.80; S, 11.09 (%).

Molecular weight: 540.72 FAB-MS m/z 541 (M +H)$^+$.

Solubility: soluble: chloroform, ethyl acetate sparingly soluble: methanol, ethanol insoluble: water, hexane.

Color reaction: positive: cerium sulfate reaction, sulfuric acid reaction, iodine vapor reaction. negative: ninhydrin reaction, ferric chloride reaction, Ehrlich reaction, Molish reaction.

Thin layer chromatography:

| Stationary phase | Developing solvent | Rf value |
| --- | --- | --- |
| silica plate* | dichloromethane:methanol (10:1) | 0.65 |

*silica plate, Kieselgel 60 F$_{254}$ (made by E. Merck)

Ultraviolet absorption spectrum: end absorption (in methanol).

Figure 1:
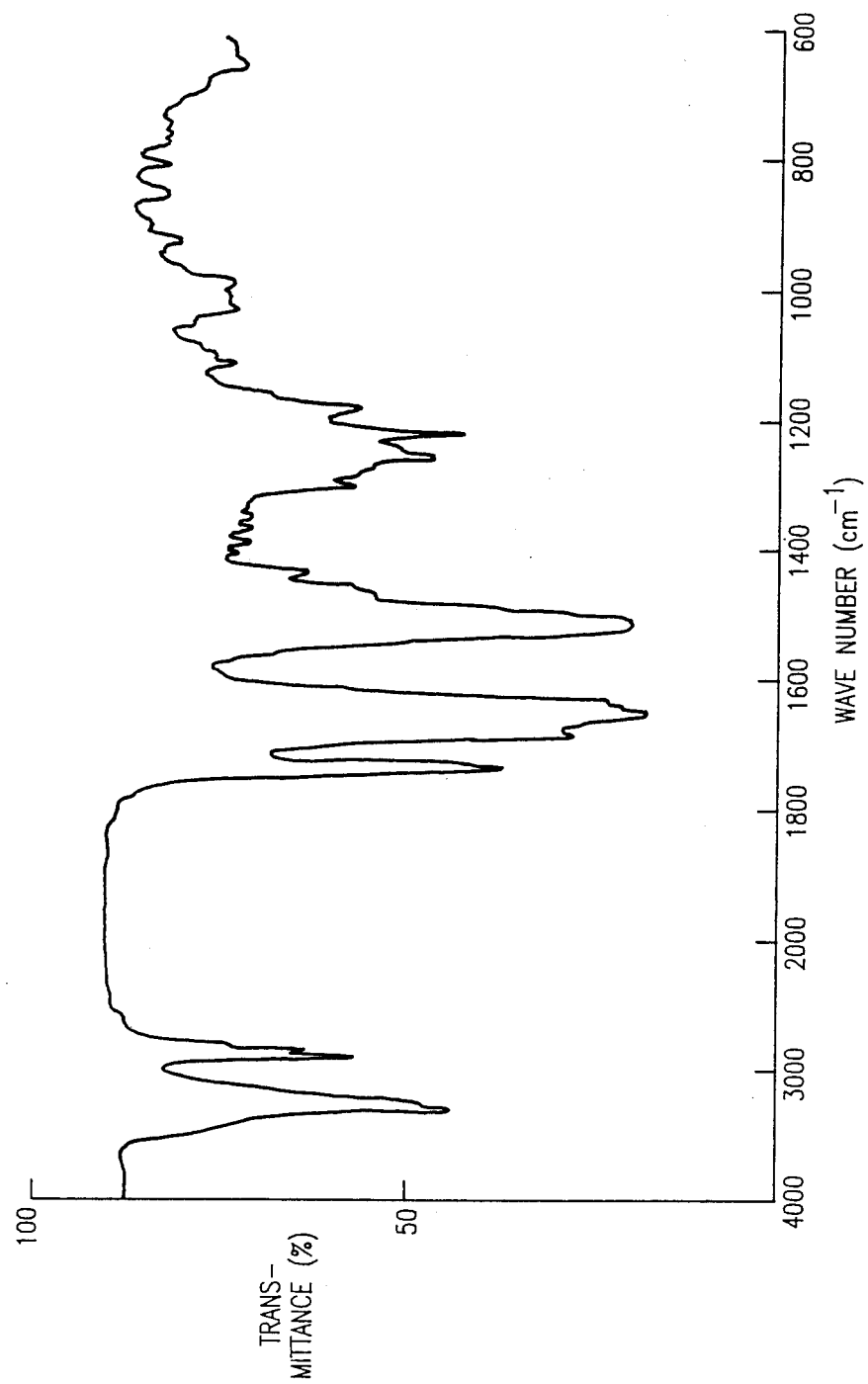
FIG. 1 illustrates its infrared absorption spectrum.

Infrared absorption spectrum: $\nu_{max}^{KBr}$=3360, 3320, 2950, 2910, 1740, 1690, 1660, 1650, 1630, 1520, 1460, 1440, 1400, 1390, 1370, 1350, 1300, 1250, 1220, 1170, 1100, 1040, 1020, 1000, 980, 910 cm$^{-1}$, as shown in FIG. 1 of the accompanying drawing.

Figure 2:
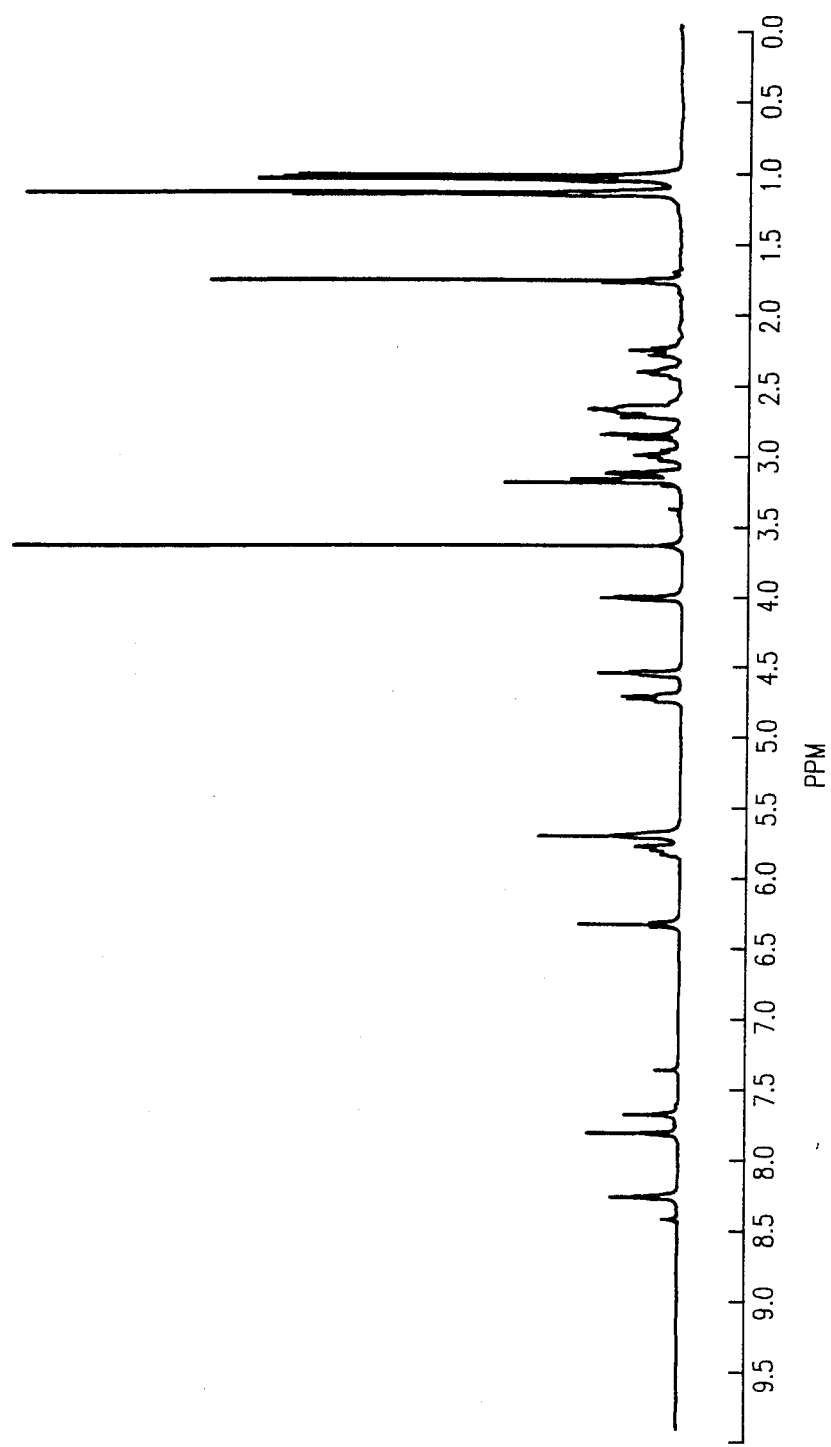
FIG. 2 illustrates its $^1$H nuclear magnetic resonance spectrum.

$^1$H Nuclear magnetic resonance spectrum: [CDCl$_3$–CD$_3$OD (10:1), 400 MHz]δ: 8.41 (1H, s, exchangeable), 8.25 (1H, d, J=4 Hz, exchangeable), 7.80 (1H, d, J=6.5 Hz, exchangeable), 7.66 (1H, d, J=8 Hz, exchangeable), 6.31 (1H, q, J=7 Hz), 5.76 (1H, m), 5.70–5.63 (2H, m), 4.69 (1H, m), 4.51 (1H, m), 3.97 (1H, dd, J=6 and 4 Hz), 3.20–3.07 (3H, m), 2.95 (1H, m), 2.83 (1H, dd, J=14 and 1.5 Hz), 2.66 (1H, dd, J=14 and 6 Hz),2.65–2.60 (2H, m), 2.37 (1H, m), 2.22 (1H, m), 1.72 (3H, d, J=6.5 Hz), 1.10 (3H, d, J=7 Hz),1.08 (3H, d, J=7 Hz), 1.00 (3H, d, J=6.5 Hz), 0.97 (3H, d, J=7 Hz) ppm, as shown in FIG. 2 of the accompanying drawing.

Figure 3:
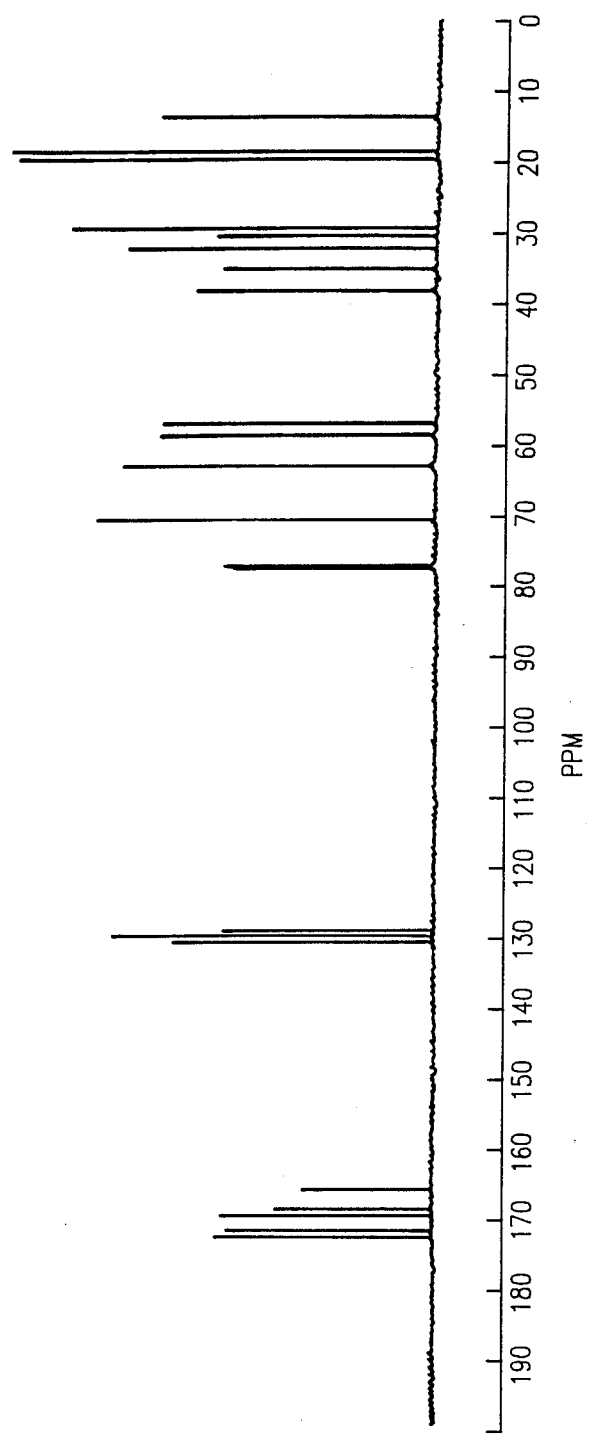
FIG. 3 illustrates its $^{13}$C nuclear magnetic resonance spectrum.

$^3$C Nuclear magnetic resonance spectrum (CDCl$_3$–CD$_3$OD (10:1), 100 MHz) δ: 172.34 (s), 171.43 (s), 169.17 (s), 168.37 (s), 165.59 (s), 130.36 (d), 129.64 (d), 129.62 (s), 129.04 (d), 70.15 (d), 62.42 (d), 58.10 (d), 56.57 (d), 37.75 (t), 37.56 (t), 34.46 (t), 31.65 (d), 30.02 (t), 28.88 (d), 19.09 (q), 18.96 (q), 18.29 (q), 18.03 (q), 13.04 (q) ppm, as shown in FIG. 3 of the accompanying drawing.

Amino acid analysis:

FR901228 substance (4 mg) was hydrolyzed at 110° C. for 20 hours with 6N hydrochloric acid (2 ml) in a sealed tube. The mixture was analyzed on an automatic amino acid analyzer. The result of the amino acid analysis on FR901228 substance revealed the presence of valine and ammonia (the ratio of valine and ammonia is 2:1).

From analysis of the physico-chemical properties including the above-mentioned data and the chemical structures of some derivatives derived from FR901228 substance, FR901228 substance is proved to have the following chemical formula:

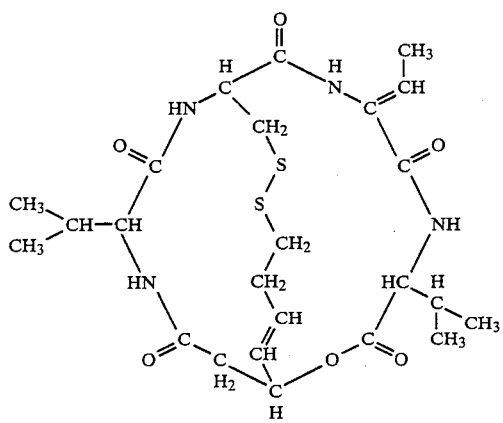

Derivatives derived from FR901228 substance:

From FR901228 substance, some derivatives were derived.

PREPARATION 1

From FR901228 substance, FR123392 substance and FR125441 substance were derived.

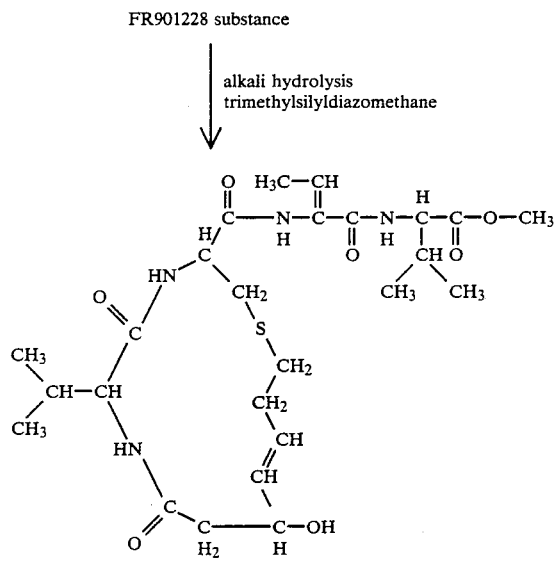

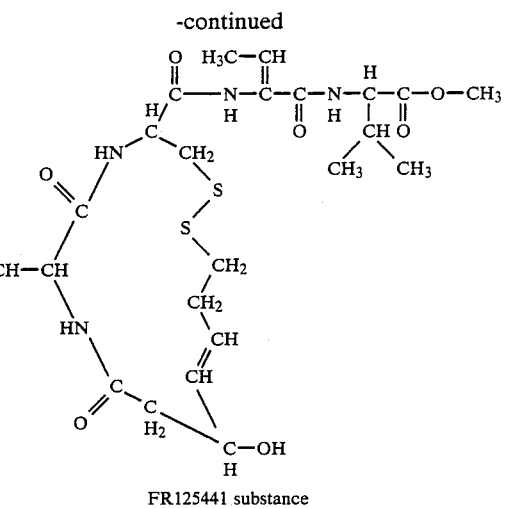

To a solution of FR901228 substance (54 mg) in methanol (2 ml) was added a 1N-aqueous solution of sodium hydroxide (200 ml). After stirring for 12 hours at room temperature, aqueous hydrogen chloride was added thereto to adjust to pH 1, and extracted with ethyl acetate. After drying over magnesium sulfate and filtration, the solvent was evaporated. The residue was dissolved in methanol and was added trimethylsilyl diazomethane (1 ml). After 5 minutes, one drop of acetic acid was added and the solvent was evaporated. The residue was purified by preparative thin layer chromatography (0.5 mm×2) and developed with 10% methanol in chloroform to give FR123392 substance (15 mg) and FR125441 substance (10 mg).

FR123392 substance:

$^1$H Nuclear magnetic resonance spectrum: [CDCl$_3$ -CD$_3$OD (10:1), 200 MHz]. δ: 0.98(12H, m), 1.75(3H, d, J=7 Hz), 2.0-2.9(10H, m), 3.05(1H, dd, J=4 and 14 Hz), 3.71(3H, s), 4.13(1H, d, J=8 Hz), 4.37(2H, m), 4.57(1H, dd, J=5 and 10 Hz), 5.6(2H, m), 6.64(1H, q, J=7 Hz), 7.48(1H, d, J=10 Hz).

Infrared absorption spectrum $\nu_{max}^{KBr}$=3260, 2920, 2400, 1720, 1620, 1510, 1430, 1260, 1200, 1010 cm$^{-1}$.

FAB-MS m/z 541 (M +H)$^+$.

FR125441 substance:

$^1$H Nuclear magnetic resonance spectrum: [CDCl$_3$ -CD$_3$OD (10:1), 400 MHz]. δ:0.95(12H, m), 1.76(3H, d, J=7 Hz), 2.20(1H, m), 2.35(3H, m), 2.7(4H, m), 2.98(1H, dd, J=13 and 8 Hz), 3.08(1H, dd, J=13 and 4.5 Hz), 3.72(3H, s), 4.14(1H, d, J=6 Hz), 4.35(1H, d, J=7 Hz), 4.43(2H, 25 m), 5.67(1H, dd, J=6 and 15 Hz), 5.78(1H, dt, J=15 and 6 Hz), 6.70(1H, q, J=7 Hz).

FAB-MS m/z 573 (M +H)$^+$.

PREPARATION 2

From FR125441 substance, FR123393 substance was derived.

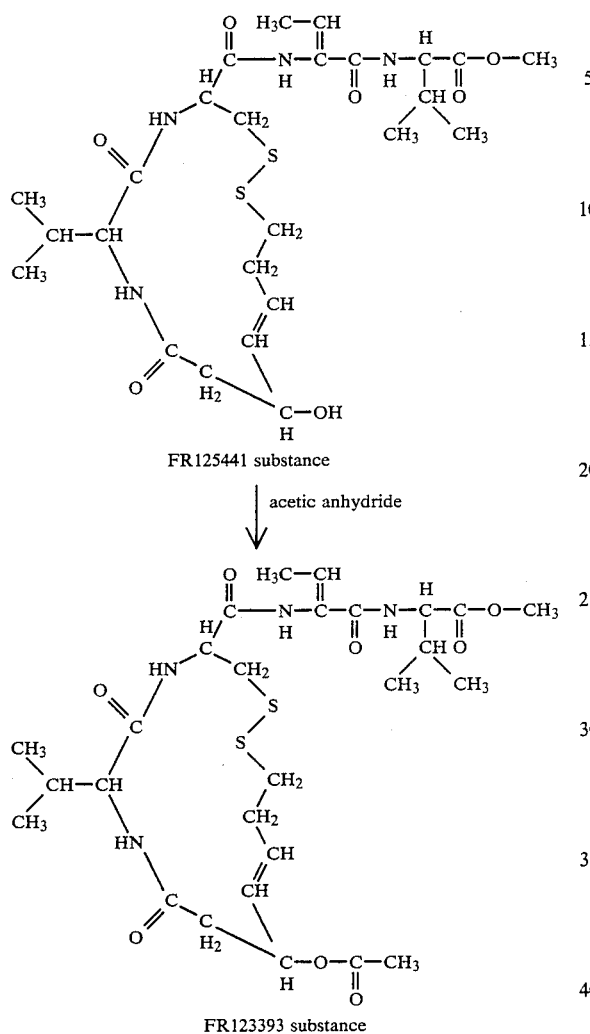

FR125441 substance

↓ acetic anhydride

FR123393 substance

To a solution of FR125441 substance (10 mg) in pyridine (0.8 ml) was added acetic anhydride (0.4 ml). After stirring for 12 hours at room temperature, solvent was evaporated. The residue was subjected to preparative thin layer chromatography (0.5 mm×1) and developed with 5% methanol in chloroform to give FR123393 substance (10 mg).

FR123393 substance:

¹H Nuclear magnetic resonance spectrum: [CDCl₃-CD₃OD (10:1), 200 MHz]δ: 1.0(12H, m), 1.75(3H, d, J=7 Hz), 2.05(3H, s), 1.9–3.3(10H, m), 3.70(3H, s), 4.20(1H, d, J=8 Hz), 4.34(1H, d, J=7 Hz), 4.84(1H, m), 5.5(2H, m), 15 5.84(1H, dt, J=15 and 7 Hz), 6.65(1H, q, J=7 Hz).

Infrared absorption spectrum: $\nu_{max}^{KBr}$ =3280, 2950, 2430, 1720, 1630, 1500, 1425, 1360, 1225, 1010, 960 cm⁻¹.

FAB-MS m/z 615 (M +H)+·

PREPARATION 3

From FR901228 substance, FR123395 substance was derived.

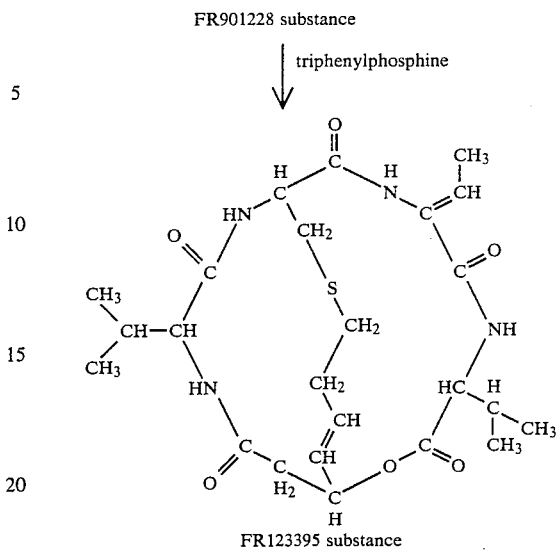

FR901228 substance

↓ triphenylphosphine

FR123395 substance

To a solution of FR901228 substance (54 mg) in dioxane (2 ml) was added a triphenylphosphine (55 mg). After stirring for 72 hours at room temperature, the solvent was removed in vacuo. The residue was subjected to preparative thin layer chromatography (0.5 mm×2) and developed with 2% methanol in chloroform to give FR123395 substance (10 mg).

FR123395 substance:

¹H Nuclear magnetic resonance spectrum: [CDCl₃ - CD₃OD (10:1), 200 MHz] δ: 1.0(12H, m), 1.5(1H, m), 1.85(3H, d, J=7 Hz), 2.1 - 3.1(9H, m), 3.90(1H, d, J=8 Hz), 4.45(1H, d, J=7 Hz), 5.65 - 6.0(4H, m), 6.24(1H, q, J=7 Hz.

Infrared absorption spectrum: KBr=3300, 2920, 2470, 1730, 1640, 1500, 1420 cm⁻¹ max Biological properties of FR901228 substance As examples for showing biological activity of FR901228 substance some biological data are explained in the following.

TEST 1

Antimicrobial activity of FR901228

Antimicrobial activity of FR901228 was performed by an agar dilution method in Sabouraud medium.

Minimum inhibitory concentration (MIC) is expressed in terms of μg/ml after 48 hours incubation at 25° C. The results is shown in Table 3.

TABLE 3

| Antimicrobial activity of FR901228 substance | |
|---|---|
| Organisms | MIC (μg/ml) |
| *Shizosaccharomyces pombe* | 10 |
| *Aureobasidium pullulans* IFO 4466 | 10 |
| *Aspergillus niger* | 100 |

TEST 2

Inhibition of human tumor cell growth in vitro by FR901228 substance

The cytotoxicity test was performed in microtiter plates, with each well containing 3×10³ tumor cells in 100 μl Dulbecco's minimum essential medium supplemented with 10% fetal calf serum, penicillin (50 units/ml) and streptomycin (50 μg/ml). The cells were incubated at 37° C. for four days and the colorimetric MTT [3-(4,5-dimethylthiazol-2-yl)-2,5-diphenyl tetrazolium bromide, made by Sigma] assay was performed according to the method described by Mosmann (J. Immunol. Methods, 65, 55–63, 1983). MTT was dissolved in phosphate buffer solution (PBS) at 5 mg/ml and filtered to sterilize and remove a small amount of insoluble residue. After the culture of human tumor cells was terminated, this MTT solution (10 μl per 100 μl medium) was added to all wells of an assay, and plates were further incubated at 37° C. for 4 hours. Acid-isopropanol (100 μl of 0.04N HCl in isopropanol) was added to all wells and mixed thoroughly to dissolve the dark blue crystals. After all crystals were dissolved, the plates were read on a 2-wavelength microplate photometer (Model MTP-22; Corona Electric Co., Ltd., Katsuta, Japan) at 550 nm, a reference wavelength of 660 nm. The object compound of this invention was dissolved in methanol and diluted in Dulbecco's minimum essential medium and added to the culture to give final concentration of 1 μg/ml or less. The result is shown in Table 4.

TABLE 4

Inhibition of human tumor cell growth in vitro by FR901228 substance

| Human tumor cell lines | $IC_{50}$ (ng/ml) |
|---|---|
| A549 (lung cancer) | 0.82 |
| MCF-7 (breast cancer) | 0.99 |
| SW480 (colon cancer) | 0.57 |

TEST 3

Antitumor activity of FR901228 substance against P388 murine leukemia

Antitumor activity of FR901228 substance was determined in murine tumor system. P388 leukemia cells ($1 \times 10^6$) were implanted intraperitoneally into BDF1 mice (female, 8 weeks old). Twenty-four hours after the inoculation of tumor cells, FR901228 substance was administered intraperitoneally to mice. Administrations of FR901228 substance were continued intraperitoneally once daily for another three days. FR901228 substance was suspended in 0.9% saline. Control mice received intraperitoneal doses of 0.9% saline.

The result is shown in Table 5. Antitumor activity was expressed as the mean survival time of group and also expressed as the T/C % (100 × treated group/control group) of mean survival time.

TABLE 5

Antitumor activity of FR901228 substance against P388 murine leukemia

| Dose (mg/kg/day) | n | Mean Survival Time (day) | Time (%) |
|---|---|---|---|
| control | 4 | 9.0 | 100 |
| 1.0 | 4 | 15.25 | 169.4 |
| 0.32 | 4 | 14.25 | 158.3 |

The pharmaceutical composition of this invention can be used in the form of a pharmaceutical preparation, for example, in solid, semisolid or liquid form, which contains FR901228 substance, as an active ingredient in admixture with an organic or inorganic carrier or excipient suitable for external, oral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. And, if necessary, in addition, auxiliary, stabilizing, thickening and coloring agents and perfumes may be used. FR901228 substance may be included in the pharmaceutical composition in an amount sufficient to produce the desired antitumor effect upon the process or condition of diseases.

For applying the composition to human, it is preferable to apply it by intravenous, intramuscular or oral administration. While the dosage of therapeutically effective amount of FR901228 substance varies from and also depends upon the age and condition of each individual patient to be treated, in the case of intravenous administration, a daily dose of 0.1–100 mg of FR901228 substance per kg weight of human being, in the case of intramuscular administration, a daily dose of 0.1–100 mg of FR901228 substance per kg weight of human being, in case of oral administration, a daily dose of 0.1–100 mg of FR901228 substance per kg weight of human being is generally given for treating tumor.

The derivatives derived from FR901228 substance as stated above have also antitumor activity.

The following examples are given for the purpose of illustrating the present invention in more detail.

EXAMPLE 1

Fermentation

A culture medium (160 ml) containing glucose (1%) and bouillon (1%) was poured into each of 500 ml Erlenmeyer flasks and sterilized at 120° C. for 30 minutes. A loopful of slant culture of *Chromobacterium violaceum* WB968 was inoculated to each of the medium and cultured at 30° C. for 24 hours on a rotary shaker. The resultant culture was inoculated to a medium containing glucose (1%), bouillon (1%) and Adekanol (deforming agent, trade mark, made by Asahi Denka Kogyo Co.) (0.05%) (15 liters) in each of twelve 30-liter jar-fermentors, which has been sterilized at 120° C. for 30 minutes in advance, and cultured at 30° C. for 24 hours under aeration of 20 liters/minute and agitation of 200 rpm.

Isolation and purification:

After the culture was terminated, each jar-fermentor was sterilized at 120° C. for 30 minutes. The culture broth thus obtained was filtered with an aid of diatomaseous earth (10 kg). The filtrate (150 liters) was extracted twice with ethyl acetate (150 liters). The extract was evaporated under reduced pressure to give an oily residue. The oily residue was mixed with 500 g of silica gel (Kiesel gel 60, 70–230 mesh, made by E. Merck), and this mixture was slurried in methanol. After evaporating the solvent, the resultant dry powder was subjected to column chromatography of the same silica gel (0.5 liter) which was packed with n-hexane. The column was developed with n-hexane (2 liters), a mixture of n-hexane and ethyl acetate (3:1 v/v, 3 liters; 1:1 v/v, 3 liters; 1:2 v/v, 3 liters) and ethyl acetate (5 liters). Fractions containing the object compound were collected and concentrated under reduced pressure to give FR901228 substance in the form of slightly yellowish powder. This powder was dissolved in a mixture of dichloromethane and methanol (10:1 v/v, 10 ml). To this solution was added acetonitrile (20 ml). This was kept at room temperature and purified FR901228 substance (920 mg) was obtained as colorless crystals.

What we claim is:

1. FR901228 substance of the following formula,

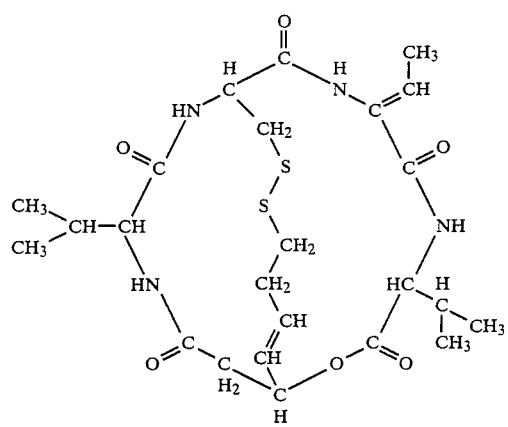
2. A pharmaceutical composition which comprises, as an active ingredient FR901228 substance as defined in claim 1 and a non-toxic, pharmaceutically acceptable carrier.
* * * * *